United States Patent [19]

Franke et al.

[11] Patent Number: 4,701,563
[45] Date of Patent: Oct. 20, 1987

[54] DIFLUOROCYCLOPROPANE DERIVATIVES AND THEIR PREPARATION, AS WELL AS PESTICIDAL COMPOSITIONS BASED ON THESE COMPOUNDS

[75] Inventors: Heinrich Franke; Hartmut Joppien; Helga Franke, all of Berlin, Fed. Rep. of Germany

[73] Assignee: Schering Aktiengesellschaft, Fed. Rep. of Germany

[21] Appl. No.: 841,861

[22] Filed: Mar. 20, 1986

[30] Foreign Application Priority Data

Apr. 9, 1985 [DE] Fed. Rep. of Germany ....... 3513041

[51] Int. Cl.$^4$ ............................................. C07C 35/04
[52] U.S. Cl. ................................... 568/639; 568/637
[58] Field of Search ............... 568/637, 639; 514/717, 514/719

[56] References Cited

U.S. PATENT DOCUMENTS 4,611,004 9/1986 Ackermann et al. ........... 568/637 X

FOREIGN PATENT DOCUMENTS 3317908 12/1983 Fed. Rep. of Germany ...... 568/639
WO84/01147 3/1984 World Int. Prop. O. .......... 568/637

OTHER PUBLICATIONS

Mitsch, Jour. Amer. Chem. Soc., vol. 87 (1965) 758–761.

*Primary Examiner*—Werren B. Lone
*Attorney, Agent, or Firm*—Ostrolenk, Faber, Gerb & Soffen

[57] ABSTRACT

Difluorocyclopropane derivatives of the general formula I

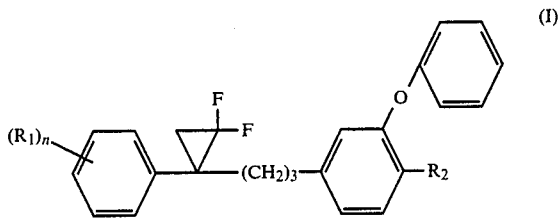

in which
$R_1$ is halogen, $C_{1-4}$-alkoxy, fluoro-substituted alkoxy, $C_{1-4}$-alkyl or trifluoromethyl,
$R_2$ is hydrogen or fluorine and
n is 0, 1 or 2, are described, which have valuable insecticidal and acaricidal properties.

19 Claims, No Drawings

DIFLUOROCYCLOPROPANE DERIVATIVES AND THEIR PREPARATION, AS WELL AS PESTICIDAL COMPOSITIONS BASED ON THESE COMPOUNDS

This invention relates to new difluorocyclopropane derivatives and their preparation, as well as pesticidal compositions based on these compounds.

Cyclopropane derivatives with insecticidal activity have been described, as for example in EP No. 94,085, EP No. 104,908 and DE No. 3,317,908. In the last specification there are described compounds of the formula

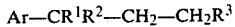

where Ar is an optionally substituted phenyl or naphthyl ring, $R^1$ is methyl, ethyl or isopropyl, $R^2$ is hydrogen or methyl or $R^1$ and $R^2$ together with the C-atom to which they are attached form an optionally substituted cycloalkyl group, and $R^3$ is the residue of an alcohol, $R^3OH$.

Among the compounds disclosed in which $R^1$ and $R^2$ form a cycloalkyl group is one which is geminally substituted by two chlorine atoms.

It has now been found that a selection of compounds in which these chlorine atoms are replaced by fluorine are distinguished by particularly valuable insecticidal and acaricidal, especially tickicidal, properties. These compounds are of formula I

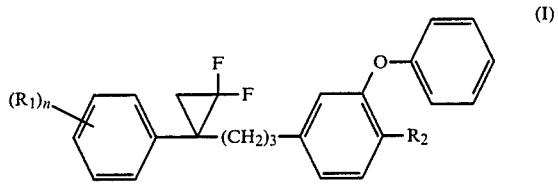

in which
$R_1$ is halogen, $C_{1-4}$-alkoxy, fluoro-substituted alkoxy, $C_{1-4}$-alkyl or trifluoromethyl,
$R_2$ is hydrogen or fluorine and
n is 0, 1 or 2.

By the term halogen is usually meant fluorine, chlorine or bromine. Alkyl and alkoxy groups can be branched or straight chained, e.g methyl, ethyl, propyl isopropyl or tert.-butyl.

Particularly preferred compounds of formula I are those in which n is 1 and $R_1$ is in the 4-position and is chlorine or ethoxy.

Examples of these compounds are
1-(4-chlorophenyl)-2,2-difluoro-1-[3-(3-phenoxyphenyl)-propyl]cyclopropane,
2,2-difluoro-1-(4-ethoxyphenyl)-1-[3-(3-phenoxyphenyl)-propyl]cyclopropane,
1-(4-chlorophenyl)-2,2-difluoro-1-[3-(4-fluoro-3-phenoxyphenyl)-propyl]cyclopropane and
2,2-difluoro-1-(4-ethoxyphenyl)-1-[3-(4-fluoro-3-phenoxyphenyl)-propyl]cyclopropane.

The compounds according to the invention can be used at a concentration of 0.0005 to 5%, preferably from 0.001 to 1%, calculated as gram active material per 100 ml of the composition.

The compounds of the invention can be used either alone or in mixture with each other or another insecticide. Optionally other plant protection or pesticidal compositions, such as for example insecticides, acaricides or fungicides can be added depending on the desired result.

An improvement in the intensity and speed of action can be obtained, for example, by addition of suitable adjuvants, such as organic solvents, wetting agents and oils. Such additives may allow a decrease in the dose.

Suitable mixture partners may include phospholipids e.g. phosphatidylcholine, hydrated phosphatidylcholines, phosphatidylethanolamine, N-acyl-phosphatidylethanolamines, phosphatidylinositol, phosphatidylserine, lysolecithin or phosphatidylglycerol. The designated active ingredients or their mixtures can suitably be used, for example, as powders, dusts. granules, solutions, emulsions or suspensions, with the addition of liquid and/or solid carriers and/or diluents and, optionally, binding, wetting, emulsifying and/or dispersing adjuvants.

Suitable liquid carriers are, for example aliphatic and aromatic hydrocarbons such as benzene, toluene, xylene, cyclohexanone, isophorone, acetophenone, dimethylsulphoxide, dimethylformamide, other mineral-oil fractions and plant oils.

Suitable solid carriers include mineral earths, e.g. tonsil, silica gel, talcum, kaolin, attapulgite, limestone, silicic acid and plant products, e.g. flours.

As surface-active agents there can be used for example calcium lignosulphonate, polyoxyethylenealkylphenyl ether, naphthalenesulphonic acids and their salts, phenolsulphonic acids and their salts, formaldehyde condensates, fatty alcohol sulphates, as well as substituted benzenesulphonic acids and their salts.

The percentage of the active ingredient(s) in the various preparations can vary within wide limits. For example, the compositions can contain about 10 to 90 percent by weight active ingredients, and about 90 to 10 percent by weight liquid or solid carriers, as well as, optionally up to 20 percent by weight of surfactant.

The agents can be applied in customary fashion, for example with water as the carrier in spray mixture volumes of approximately 100 to 3,000 l/ha. The agents can be applied using low-volume or ultra-low-volume techniques or in the form of so-called microgranules.

The preparation of these formulations can be carried out in a known manner, for example by milling or mixing processes. Optionally, individual components can be mixed just before use for example by the so-called commonly used tank-mixing method.

Formulations can be prepared, for example, from the following ingredients.

A. 80 percent by weight active ingredient
  15 percent by weight kaolin
  5 percent by weight surface-active agent based on the sodium salt of N-methyl-N-oleyltaurine and the calcium lignosulphonate
B. 45 percent by weight active ingredient
  5 percent by weight sodium aluminium silicate
  15 percent by weight cetylpolyglycol ether with 8 moles ethylene oxide
  2 percent by weight spindle oil
  10 percent by weight polyethylene glycol
  23 parts water
C. 20 percent by weight active ingredient
  35 percent by weight bentonite
  8 percent by weight calcium lignosulphonate
  2 percent by weight of the sodium salt of N-methyl-N-oleyltaurine
  35 percent by weight silicic acid
D. 20 percent by weight active ingredient 75 percent by weight isophorone 5 percent by weight of an emulsifier mixture of calcium phenylsulphonate and fatty alcohol polyglycol ether The compounds of the invention can be prepared by reacting a compound of general formula II

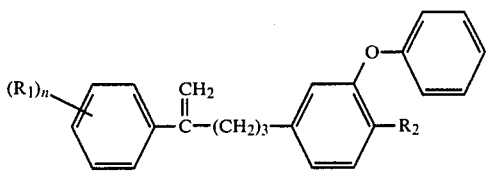

in which $R_1$, $R_2$ and n have the meanings given above, with difluorocarbene.

The process can suitably be carried out in such a way that the difluorocarbene is formed in situ. In principle any suitable known method can be used to prepare the difluorocarbene. A preferred method is by preparation from sodium chlorodifluoroacetate dissolved in diglyme at c.165° C. in the solution of the starting materials.

Other polar solvents that do not react with difluorocarbene can also be used, such as dimethylformamide or sulpholane.

The starting material of general formula II can be prepared in a three stage synthesis. In the first stage a nitrile of formula

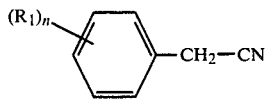

is treated with an alkylating agent of formula

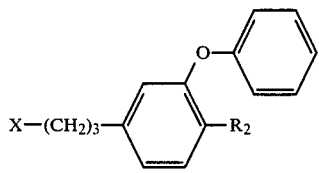

in the presence of a base.

In the second stage the condensation product thus obtained is oxidised with atmospheric oxygen in the presence of an alkali metal hydroxide whereby the cyano group is converted to a keto group and following this, in the third stage, the ketone is treated with triphenylmethylenephosphorane in a Wittig reaction to give the exo methylene compound.

$R_1$, $R_2$ and n have the meanings given in formula I and X is a leaving group such as Cl, Br, mesylate or tosylate.

The following examples illustrate the preparation of compounds according to the invention.

EXAMPLE 1

1-(4-Chlorophenyl)-2,2-difluoro-1-[3-(4-fluoro-3-phenoxyphenyl)propyl]cyclopropane 3.0 g (20 mmol) Sodium chlorodifluoroacetate, dissolved in 15 ml diglyme, was added dropwise over 60 minutes to a boiling solution (bath temperature 200° C.) of 2.76 g (7.5 ml) 2-(4-chlorophenyl)-5-(4-fluoro-3-phenoxyphenyl)-1-pentene in 15 ml diglyme. The mixture was then heated for 30 minutes, after which it was cooled, poured into water, extracted three times with ether, the extracts washed with water and dried over magnesium sulphate. The evaporated residue was chromatographed on 100 g silica gel, using a mixture of ether and hexane (1:9). After evaporation, 2.8 g of product remained (90% of theory).

$n_D^{20}$: 1.5598 The starting material was obtained as follows.

1.

2-(4-chlorophenyl)-5-(4-fluoro-3-phenoxyphenyl)-valeronitrile

To a stirred mixture of 30.6 g (0.2 mol) of 4-chlorobenzonitrile. 50 ml aqueous sodium hydroxide (50%) and 0.5 g tetrabutylammonium bromide was added dropwise 23.2 g (0.075 mol) of 1-bromo-3-(4-fluoro-3-phenoxyphenyl)propane. Th temperature was maintained at 30° C. by cooling. After heating for three hours, the mixture was poured into ice-water, extracted twice with ether, the extract washed with water, dried over magnesium sulphate and evaporated. Excess benzonitrile was distilled in a rotary evaporator at 150° C. and 0.1 Torr. It was then treated to silica-gel chromatography.

Yield: 27.0 g=95% of theory $n_D20$: 1.5752

2.

1-(4-chlorophenyl)-4-(4-fluoro-3-phenoxyphenyl)butan-1-one 27.0 g (0.071 mol) of the preceding nitrile, 220 ml toluene, 220 ml aqueous sodium hydroxide and 1.5 g benzyltriethylammonium chloride were stirred at room temperature whilst passing in air. The reaction finished after 2.5 hours. The mixture was then poured into ice-water, extracted three times with ether, the organic phase then washed with water and dried. The evaporated residue showed a single spot on a TLC plate and was used in the next stage without purification.

Yield: 18.9 g=72% of theory.

3.

1-(4-chlorophenyl)-4-(4-fluoro-3-phenoxyphenyl)-1-pentene 4.2 g (0.095 mol) of a 55% sodium hydride dispersion, freed from oil by several washings with toluene, was treated with 150 ml DMSO. The mixture was heated to 80° C. until it all solid material had dissolved (c. 30 mins.). 36.5 g (0.09 mol) of methyltriphenylphosphonium iodide was added at room temperature and the mixture stirred until all solid material had dissolved. Then 18.8 g (0.051 mol) of the ketone, dissolved in 50 ml DMSO, was added dropwise and stirred at room temperature for 12 hours. The mixture was then poured into ice-water, extracted three times with ether, the organic phase then washed with water and dried over magnesium sulphate. The evaporated residue was treated to silica-gel chromatography.

Yield: 12.6 g=68% of theory $n_D20$: 1.5898

In a similar manner the following compounds according to the invention were prepared.

| Example No. | Compound | Physical constant $n_D^{20}$ |
|---|---|---|
| 2 | 1-(4-chlorophenyl)-2,2-difluoro-1-[3-(3-phenoxyphenyl)propyl]cyclopropane | 1.5672 |
| 3 | 2,2-difluoro-1-(4-ethoxyphenyl)-1-[3-(3-phenoxyphenyl)propyl]cyclopropane | 1.5580 |
| 4 | 2,2-difluoro-1-(4-ethoxyphenyl)-1-[3-(4-fluoro-3-phenoxyphenyl)propyl]cyclopropane | 1.5492 |
| 5 | 2,2-difluoro-1-(4-methoxyphenyl)-1-[3-(3-phenoxyphenyl)propyl]cyclopropane | 1.5623 |
| 6 | 2,2-difluoro-1-(4-difluoromethoxyphenyl)-1-[3-(4-fluoro-3-phenoxyphenyl)propyl]cyclopropane | 1.5325 |
| 7 | 2,2-difluoro-1-[3-(4-fluoro-3-phenoxyphenyl)propyl]-1-(4-methoxyphenyl)cyclopropane | 1.5546 |
| 8 | 2,2-difluoro-1-[4-(2-fluoroethoxy)phenyl]-1-[3-(4-fluoro-3-phenoxyphenyl)propyl]cyclopropane | 1.5470 |
| 9 | 2,2-difluoro-1-(4-fluorophenyl)-1-[3-(4-fluoro-3-phenoxyphenyl)propyl]cyclopropane | 1.5433 |
| 10 | 1-(4-bromophenyl)-2,2-difluoro-1-[3-(4-fluoro-3-phenoxyphenyl)propyl]cyclopropane | 1.5695 |
| 11 | 2,2-difluoro-1-[3-(4-fluoro-3-phenoxyphenyl)propyl]-1-(4-trifluoromethylphenyl)cyclopropane | 1.5220 |
| 12 | 2,2-difluoro-1-[3-(4-fluoro-3-phenoxyphenyl)propyl]-1-(4-prop-2-yloxyphenyl)cyclopropane | 1.5466 |
| 13 | 2,2-difluoro-1-[3-(4-fluoro-3-phenoxyphenyl)propyl]-1-(4-propyloxyphenyl)cyclopropane | 1.5449 |
| 14 | 1-(4-butoxyphenyl)-2,2-difluoro-1-[3-(4-fluoro-3-phenoxyphenyl)propyl]cyclopropane | 1.5412 |
| 15 | 2,2-difluoro-1-[3-(4-fluoro-3-phenoxyphenyl)propyl]-1-(4-methylphenyl)cyclopropane | 1.5501 |
| 16 | 1-(3,4-dichlorophenyl)-2,2-difluoro-1-[3-(4-fluoro-3-phenoxyphenyl)propyl]cyclopropane | 1.5673 |
| 17 | 2,2-difluoro-1-(3-fluoro-4-methoxyphenyl)-1-[3-(4-fluoro-3-phenoxyphenyl)propyl]cyclopropane | 1.5468 |
| 18 | 2,2-difluoro-1-(4-ethoxy-3-fluorophenyl)-1-[3-(4-fluoro-3-phenoxyphenyl)propyl]cyclopropane | 1.5432 |
| 19 | 2,2-difluoro-1-[4-(2-fluoroethoxy)-3-fluorophenyl]-1-[3-(4-fluoro-3-phenoxyphenyl)propyl]cyclopropane | 1.5409 |
| 20 | 2,2-difluoro-1-phenyl-1-[3-(3-phenoxyphenyl)propyl]cyclopropane | 1.5643 |
| 21 | 2,2-difluoro-1-(4-ethylphenyl)-1-[3-(3-phenoxyphenyl)propyl]cyclopropane | 1.5589 |
| 22 | 2,2-difluoro-1-(4-propylphenyl)-1-[3-(3-phenoxy-phenyl)propyl]cyclopropane | 1.5595 |
| 23 | 2,2-difluoro-1-(4-tert.-butylphenyl)-1-[3-(3-phenoxy-phenyl)propyl]cyclopropane | 1.5427 |
| 24 | 2,2-difluoro-1-phenyl-1-[3-(4-fluoro-3-phenoxyphenyl)propyl]cyclopropane | 1.5513 |
| 25 | 2,2-difluoro-1-(4-ethylphenyl)-1-[3-(4-fluoro-3-phenoxyphenyl)propyl]cyclopropane | 1.5462 |
| 26 | 2,2-difluoro-1-(4-propylphenyl)-1-[3-(4-fluoro-3-phenoxyphenyl)propyl]cyclopropane | 1.5482 |
| 27 | 2,2-difluoro-1-(4-tert.-butoxyphenyl)-1-[3-(4-fluoro-3-phenoxyphenyl)propyl]cyclopropane | 1.5229 |

TEST EXAMPLE 1

Activity against larvae (L3) of the Mexican bean beetle (*Epilachna varivestis*)

Compounds were made up as aqueous emulsions at a concentration of 0.0064%. French bean plants (*Phaseolus vulgaris*) in the primary leaf stage were dipped in the preparations. For each test two plant stems with 4 primary leaves were placed in glass vases filled with water and enclosed in plexiglass cylinders. Then 5 larvae of the Mexican bean beetle (*Epilachna varivestis*) at the third larval stage were put in the glass cylinders and kept for 3 days. The % mortality of the larvae after 3 days indicated the level of activity.

The compounds of Examples 1–12, 14–18 and 20–22 showed 100% activity (mortality), whereas 2,2-dichloro-1-(4-chlorophenyl)-1-[3-(3-phenoxyphenyl)propyl]cyclopropane (compound No. 50 of DE 33 17 908) showed only 90% activity.

TEST EXAMPLE 2

Activity against larvae of diamond-backed moth (*Plutella xylostella*).

The compounds were made up as aqueous emulsions at a concentration of 0.0064%. Cabbage leaves, placed in polystyrene petri dishes, were sprayed with these preparations (4 mg spray/cm$^2$). After the sprayed surface had dried, 10 young larvae of the diamond-backed moth (*Plutella xylostella*) were placed in each petri dish and thereby exposed to the treated food in the closed dishes for two days. The % mortality of the larvae after two days indicated the level of activity. The results are summarised in the following table.

The compounds of Examples 1, 2, 4–7, 9–11, 15, 16, 18 and 19 showed 100% activity (mortality), whereas compound No. 50 of DE No. 33 17 908 showed only 20% activity.

TEST EXAMPLE 3

Activity against larvae (L2) of the cotton army worm (*Spodoptera littoralis*)

Compounds were made up as aqueous emulsions at a concentration of 0.0064%. Leaflet pairs of beans (*Vicia fabae*) as well as 10 larvae (L2) of the cotton army worm (*Spodoptera littoralis*) per experiment were sprayed with 4 mg spray/cm$^2$ of these preparations in polystyrene petri dishes. The closed petri dishes were left in the laboratory under extended daylight conditions for two days. The % mortality of the larvae after two days indicated the level of activity.

The compounds of Examples 1–5, 7–9, 11–13, 15, and 17–19 showed 100% activity (mortality), whereas compound No. 50 of DE No. 33 17 908 showed no (0%) activity.

TEST EXAMPLE 4

Activity against motile stages and eggs of the two spotted spider mite (*Tetranychus urticae*).

Compounds of the invention were made up to an aqueous emulsion at a concentration of 0.1%. Dwarf bean plants (*Phaseolus vulgaris*) in the primary leaf stage, which had been infested with spider mites (*Tetranychus urticae*), were sprayed with these preparations until they were dripping wet and left in a laboratory for seven days. After this the % mortality of the motile stages on the one hand and the eggs on the other hand were estimated using a magnifying glass.

The results are shown in the following table.

| Compounds of Example No | Activity in % against *Tetranychus urticae* motile stages/eggs | |
|---|---|---|
| 1 | 100 | 0 |
| 2 | 86 | 0 |
| 3 | 84 | 0 |
| 4 | 100 | 100 |
| 6 | 90 | 96 |
| 7 | 100 | 100 |
| 8 | 90 | 90 |
| 9 | 100 | 48 |
| 10 | 100 | 0 |
| 11 | 100 | 90 |
| 12 | 100 | 90 |
| 13 | 100 | 50 |
| 14 | 90 | 0 |

| Compounds of Example No | Activity in % against Tetranychus urticae motile stages/eggs | |
| --- | --- | --- |
| 15 | 82 | 0 |
| 16 | 82 | 0 |
| 18 | 100 | 100 |
| 19 | 100 | 100 |
| COMPARISON | | |
| Compound 50 of DE 3,317,908 | 0 | 0 |

TEST EXAMPLE 5

Insecticidal and acaricidal activity against *Boophilus microplus* (1), *Lucilia sericata* (2) *Musca domestica* (3) and *Blattella germanica* (4).

1. 9 cm diameter filter papers were impregnated with 1 ml aliquots of acetone solutions of test compound at various concentrations. The papers were allowed to dry and then folded into envelopes in which cattle tick larvae, (*Boophilus microplus*) were enclosed and held at 25° C. and 80% R. H. for 48 hours. The percentage mortality of tick larvae was then recorded and compared with controls.

The controls gave a mortality of less than 5% whereas compounds of Examples 1–17 caused 90% mortality at a concentration of 100 ppm or less.

2. 1 ml aliquots of an acetone solution containing test compound at various concentrations were applied to cotton wool dental rolls 1 cm×2 cm, contained in glass vials (2 cm diameter×5 cm long). After drying, the treated materials were then impregnated with 1 ml of nutrient solution, infested with first instar larvae of sheep blow fly (*Lucilia sericata*), closed by a cotton wool plug and held at 25° C. for 24 hours. For the controls the mortality was <5% whereas the compounds of Examples 1, 3–4 and 16–19 had an $LC_{90}$ of 100 ppm or less.

3. Aliquots of acetone solutions of test compounds at various concentrations were applied to 9 cm diameter filter papers placed in the bottom of 9 cm diameter petri dishes closed by glass lids. After evaporation of solvent, the treated surfaces, together with control treated with acetone alone, were then infested with adult houseflies, (*Musca domestica*) and held at 22° C. for 24 hours.

The percentage mortality of the insects was then recorded. Less than 5% mortality resulted in the control treatments whereas the compounds of Examples 1, 3, 4, 6, 9–13 and 16 had an $LD_{90}$ of 400 mg/m² or less.

4. Aliquots of acetone solutions of test compounds at various concentrations were applied to glass plates (10 cm×10 cm). After evaporation of solvent, the treated surfaces, together with controls treated with acetone alone, were then infested with second instar nymphs of the German cockroach, (*Blattella germanica*), retained on the treated surface within PTFE-coated glass rings 6 cm in diameter and held for 24 hours at 22° C. The percentage mortality of the insects was then recorded.

Less than 5% mortality resulted in the control treatments whereas the compounds of Examples 1–18 had an $LD_{90}$ of 100 mg/m² or less.

We claim:

1. Difluorocyclopropane derivatives of the general formula I

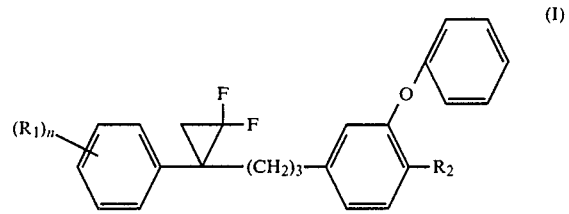

in which
 $R_1$ is halogen, $C_{1-4}$-alkoxy, fluoro-substituted alkoxy, $C_{1-4}$-alkyl or trifluoromethyl,
 $R_2$ is hydrogen or fluorine and
 n is 0, 1 or 2.

2. Difluorocyclopropane derivatives according to claim 1, wherein n is 1 and $R_1$ is in the 4-position and is chlorine or ethoxy.

3. 1-(4-Chlorophenyl)-2,2-difluoro-1-[3-(3-phenoxyphenyl)propyl]cyclopropane according to claim 1.

4. 2,2-Difluoro-1-(4-ethoxyphenyl)-1-[3-(3-phenoxyphenyl)propyl]cyclopropane according to claim 1.

5. 1-(4-Chlorophenyl)-2,2-difluoro-1-[3-(4-fluoro-3-phenoxyphenyl)-propyl]cyclopropane according to claim 1.

6. 2,2-Difluoro-1-(4-ethoxyphenyl)-1-[3-(4-fluoro-3-phenoxyphenyl)propyl]cyclopropane according to claim 1.

7. Pesticidal compositions characterised in that they comprise at least one compound according to claim 1.

8. Pesticidal composition according to claim 7 in admixture with diluent and/or carriers.

9. A method for the control of pests which comprises applying thereto or to the locus thereof an effective pesticidal amount of at least one compound according to claim 1.

10. A method according to claim 9 wherein said compound is one in which n is 1 and $R_1$ is in the 4-position and is chlorine and epoxy.

11. A method according to claim 9 wherein said compound is selected from the group consisting of 1-(4-chlorophenyl)-2,2-difluoro-1-[3-(3-phenoxyphenyl)-propyl]cyclopropane, 2,2-difluoro-1-(4-ethoxyphenyl)-1-[3-(3-phenoxyphenyl)-propyl]cyclopropane, 1-(4-chlorophenyl)-2,2-difluoro-1-[3-(4-fluoro-3-phenoxyphenyl)-propyl]cyclopropane, and 2,2-difluoro-1-(4-ethoxyphenyl)-1-[3-(4-fluoro-3-phenoxyphenyl)-propyl]cyclopropane.

12. A method according to claim 9 wherein said compound is selected from the group consisting of 2,2-difluoro-1-[3-(4-fluoro-3-phenoxy-phenyl)propyl]-1-(4-methoxyphenyl)cyclopropane, 2,2-difluoro-1-(4-fluorophenyl)-1-[3-(4-fluoro-3-phenoxyphenyl)propyl]cyclopropane, 2,2-difluoro-1-[3-(4-fluoro-3-phenoxyphenyl)-propyl]-1-4-trifluoromethylphenyl)cyclopropane, 2,2-difluoro-1-(4-ethoxy-3-fluorophenyl)-1-[3-(4-fluoro-3-phenoxyphenyl)propyl]cyclopropane.

13. Pesticidal composition according to claim 8 wherein said compound is one in which n is 1 and $R_1$ is in the 4-position and is chlorine and epoxy.

14. Pesticidal composition according to claim 8 wherein said compound is selected from the group consisting of 1-(4-chlorophenyl)-2,2-difluoro-1-[3-(3-phenoxyphenyl)propyl]cyclopropane, 2,2-difluoro-1-(4-ethoxyphenyl)-1-[3-(3-phenoxyphenyl)-propyl]cyclopropane, 1-(4-chlorophenyl)-2,2-difluoro-1-[3-(4-fluoro-3-phenoxyphenyl)-propyl]cyclopropane, and 2,2-difluoro-1-(4-ethoxyphenyl)-1-[3-(4-fluoro-3-phenoxyphenyl)-propyl]cyclopropane.

15. Pesticidal composition according to claim 8 wherein said compound is selected from the group consisting of 2,2-difluoro-1-[3-(4-fluoro-3-phenoxyphenyl)propyl]-1-(4-methoxyphenyl)cyclopropane, 2,2-difluoro-1-(4-fluorophenyl)-1-[3-(4-fluoro-3-phenoxyphenyl)propyl]cyclopropane, 2,2-difluoro-1-[3-(4-fluoro-3-phenoxyphenyl)-propyl]-1-(4-trifluoromethylphenyl)cyclopropane, 2,2-difluoro-1-(4-ethoxy-3-fluorophenyl)-1-[3-(4-fluoro-3 phenoxyphenyl)propyl]-cyclopropane.

16. 2,2-Difluoro-1-[3-(4-fluoro-3-phenoxyphenyl)-propyl]-1-(4-methoxyphenyl)cyclopropane, according to claim 1.

17. 2,2-Difluoro-1-(4-ethoxyphenyl)-1-[3-(3-phenoxyphenyl)-propyl]cyclopropane, according to claim 1.

18. 1-(4-Chlorophenyl)-2,2-difluoro-1-[3-(4-fluoro-3-phenoxyphenyl)-propyl]cyclopropane, according to claim 1.

19. 2,2-Difluoro-1-(4-ethoxy-3-fluorophenyl)-1-[3-(4-fluoro-3-phenoxyphenyl)propyl]cyclopropane according to claim 1.

* * * * *